United States Patent
Sprecker et al.

(10) Patent No.: US 6,495,186 B1
(45) Date of Patent: Dec. 17, 2002

(54) USE OF 4-ETHYLOCTANAL IN PERFUME AND FLAVOR COMPOSITIONS

(75) Inventors: Mark A. Sprecker, Sea Bright, NJ (US); Richard Anthony Weiss, Livingston, NJ (US); Manfred Pawlak, Princeton, NJ (US); John Reynolds Wright, Princeton, NJ (US); Martin Ongteco, Teaneck, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 10/153,505

(22) Filed: May 21, 2002

Related U.S. Application Data

(63) Continuation-in-part of application No. 09/964,830, filed on Sep. 26, 2001.

(51) Int. Cl.⁷ .............................. A23L 1/231; A23L 2/56
(52) U.S. Cl. ....................................................... 426/534
(58) Field of Search ............................ 426/534; 512/27

(56) References Cited

U.S. PATENT DOCUMENTS

| | | | |
|---|---|---|---|
| 4,534,891 A | | 8/1985 | Boden et al. |
| 4,922,028 A | * | 5/1990 | Oswald et al. .............. 568/448 |
| 6,110,520 A | | 8/2000 | He et al. |
| 6,333,180 B1 | | 12/2001 | Farbood et al. |

FOREIGN PATENT DOCUMENTS

WO    WO 00/33956    *    6/2000

OTHER PUBLICATIONS

Weitzel, et al, "Additional Tumor–Inhibiting Compound Classes, V[1–4] Cytostatic Properties of Alkyl–Branched Alcohols and Aldehydes with a Chain Length of C8", Institute of Physiological Chemistry of Tubingen University, Z.Physiol.Chem., 353:641–653, Apr. 1972.

* cited by examiner

*Primary Examiner*—John Hardee
(74) *Attorney, Agent, or Firm*—Joseph F. Leightner

(57) ABSTRACT

The use of 4-ethyloctanal as a flavor or fragrance chemical, suitable for use in creating fragrance and scents in items such as perfumes, colognes and personal care products, as well as a flavor ingredient for various products is disclosed.

7 Claims, No Drawings

USE OF 4-ETHYLOCTANAL IN PERFUME AND FLAVOR COMPOSITIONS

RELATED APPLICATIONS

This application is a continuation-in-part of U.S. Ser. No. 09/964,830, filed on Sep. 26, 2001, the contents of which are incorporated by reference as if set forth herein in its entirety.

FIELD OF THE INVENTION

The use of 4-ethyloctanal is disclosed as a fragrance and flavor chemical suitable for incorporation in fine fragrances, cosmetics, toiletries, food products and related applications.

BACKGROUND OF THE INVENTION

There is an ongoing need in the fragrance and flavor industry to provide new chemicals to give perfumers and other persons ability to create new fragrances for perfumes, colognes and personal care products. There is a similar ongoing need for flavor chemicals that enhance or provide new flavors for food preparations.

The preparation of the compound 4-ethyloctanal is disclosed by Weitzel, G. et al; HSZPZAZ; Hoppe-Seyler's Z. Physiol.Chem.; GE; 353; 1972, pages 641–653. The authors disclose the preparation of the compound by the dehydrogeneration of the corresponding alcohol to the aldehyde. This article is silent as to odor of the compound or the suitability of the compound to be employed as a fragrance chemical.

SUMMARY OF THE INVENTION

The present invention is directed to the use of 4-ethyloctanal as a fragrance chemical to enhance fragrance in perfumes, toilet waters, colognes, personal products and the like. More specifically, the present invention is a method for enhancing a perfume by incorporating an olfactory acceptable amount of compounds of the formula:

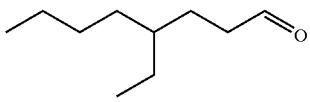

In a second embodiment, the present invention provides the use of 4-ethyloctanal in an olfactory effective amount to food products to enhance the flavor of the food.

These and other embodiments of the present invention will be apparent by reading the following specification.

DETAILED DESCRIPTION OF THE INVENTION

The present invention is directed to the use of the compound, 4-ethyloctanal in fragrance and flavor formulations. The preparation of the compound, 4-ethyl-octanal is described in Weitzel, G. et al; HSZPZAZ; Hoppe-Seyler's Z. Physiol.Chem.; GE; 353; 1972, pages 641–653.

We have discovered that 4-ethyloctanal has an orange, costus odor or note, that is well suited for use as a fragrance chemical.

The use of this compound is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, and the like.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

As used herein flavor effective amount is understood to mean the amount of compound in flavor compositions the individual component will contribute to its particular olfactory characteristics, but the flavor effect of the perfume composition will be the sum of the effects of each of the perfume or fragrance ingredients. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of 4-ethyloctanal used in flavor compositions is greater than 100 parts per trillion, generally provided at a level of from about 150 to about 10 parts per billion in the finished food product, more preferably from about 500 parts per trillion to about 5 parts per billion. The compound has been found to enhance the flavors at levels greater than about 100 parts per trillion, including uses to enhance the flavor of fruit flavors such as strawberry or raspberry at levels as low as about 200 to about 500 parts per trillion by weight. Another preferred use of the compound of the present invention is with citrus products at levels of from about 1 to about 10 parts per billion. In meat products levels of from about 1 to about 5 parts per billion were found to enhance the meat flavor.

The term "foodstuff" as used herein includes both solid and liquid ingestible materials for man or animals, which materials usually do, but need not, have nutritional value. Thus, foodstuffs include meats, gravies, soups, convenience foods, malt, alcoholic and other beverages, milk and dairy products, seafoods, including fish, crustaceans, mollusks and the like, candies, vegetables, cereals, soft drinks, snacks, dog and cat foods, other veterinary products and the like.

When the compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the 4-ethyloctanal of our invention; (2) that they be organoleptically compatible with the 4-ethyloctanal derivative(s) of our invention whereby the flavor of the ultimate consumable material to which the 4-ethyloctanal are added is not detrimentally affected by the use of the adjuvant; and (3) that they be ingestibly acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones (other than the 4-ethyloctanal derivatives of our invention) and aldehydes; lactones; other cyclic organic materials including benzene derivatives, alicyclic compounds, heterocyclics such as furans, pyridines, pyrazines and the like; sulfur-containing compounds including thiols, sulfides, disulfides and the like; proteins; lipids, carbohydrates; so-called flavor potentiators such as mono-sodium glutamate; magnesium glutamate, calcium glutamate, guanylates and inosinates; natural flavoring materials such as cocoa, vanilla and caramel; essential oils and extracts such as anise oil, clove oil and the like and artificial flavoring materials such as vanillin, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimethoxyphenol;amyl acetate; amyl cinnamate; γ-butyryl lactone; furfural; trimethyl pyrazine; phenyl acetic acid; isovaleraldehyde; ethyl maltol; ethyl vanilin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyehtyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium gulatamate; monopotassium glutamate; sulfur-containing amino acids, e.g., cysteine; hydrolyzed vegetable protein; 2-methylfuran-3-thiol;2-methyldihydrofuran-3-thiol; 2,5-dimethylfuran-3-thiol; hydrolyzed fish protein; tetramethyl pyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolne; and 4-methyl-2-(methylthiomethyl)-1,3-dithiolane. These and other flavor ingredients are provided in U.S. Pat. Nos. 6,110,520 and 6,333,180 hereby incorporated by reference.

The 4-ethyloctanal derivative(s) of our invention or compositions incorporating them, as mentioned above, can be combined with one or more vehicles or carriers for adding them to the particular product. Vehicles can be edible or otherwise suitable materials such as ethyl alcohol, propylene glycol, water and the like, as described supra. Carriers include materials such as gum arabic, carrageenan, xanthan gum, guar gum and the like.

4-Ethyloctanal prepared according to our invention can be incorporated with the carriers by conventional means such as spray-drying, drum-drying and the like. Such carriers can also include materials for coacervating the 4-ethyloctanal of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of 4-ethyloctanal derivative(s) utilized should be sufficient to impart the desired flavor characteristic to the product, but on the other hand, the use of an excessive amount of 4-ethyloctanal is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the pre-consumption treatment such as baking, frying and so on, given to the product by the ultimate consumer. Accordingly, the terminology "effective amount" and "sufficient amount" is understood in the context of the present invention to be quantitatively adequate to alter the flavor of the foodstuff.

The following are provided as specific embodiments of the present invention. Other modifications of this invention will be readily apparent to those skilled in the art, without departing from the scope of this invention. As used herein, both specification and following examples all percentages are weight percent unless noted to the contrary. IFF as used in the examples is understood to mean International Flavors & Fragrances Inc., DPG is understood to mean dipropylene glycol, DEP is understood to mean diethylphthalate.

EXAMPLE 1

Incorporation of a 4-ethyloctanal in a fragrance formulation:

| Material | Parts |
| --- | --- |
| TRIPLAL (IFF) | 4.5 |
| AMBRETTOLIDE 1% in DPG (IFF) | 30 |
| ARTEMISIA oil (Robertet) | 5 |
| BOISAMBRENE FORTE 10% in DPG (Henkel) | 90 |
| Citronellol Coeur | 40 |
| Alpha-damascone 10% DEP (Firmenich) | 1 |
| Dimethyl benzyl carbinyl butyrate | 2 |
| DPG | 88 |
| 4-Ethyloctanal | 20 |
| FLOROL (Firmenich) | 6 |
| FRUCTONE (IFF) | 11 |
| DYNASCONE 1% (DPG) | 60 |
| Ginger Chinese extract | 1 |
| Iso Cyclo Citral 10% in DPG (IFF) | 1 |
| KOAVONE (IFF) | 36 |
| LIFFAROME "PFG" 10% in DPG (IFF) | 40 |
| Litsea cubeba oil | 15 |
| MAGNOLAN (H & R) | 9 |
| Magnolia flower oil 10% in DEP | 4 |
| OXANE 1% in DPG (Firmenich) | 5 |
| Phenyl acetaldehyde | 2.5 |
| Phenyl ethyl alcohol | 130 |
| Rose oxide 10% in DPG | 13 |
| TRIFERNAL (Firmenich) | 1 |
| VELOUTONE 10% in DPG (Firmenich) | 25 |

The above formulation was described as having a green, floral note, partially through the incorporation of the 4-ethyloctanal.

The above fragrance formulations are presented to demonstrate the effectiveness of the compounds of the present invention in enhancing, improving or modifying the performance of the formulations in which they are incorporated.

EXAMPLE 2

A commercially available raspberry flavor [IFF] was tested with and without the inclusion of 4-ethyloctanal in the flavor. The compound was included as a liquid [0.05% in sugar water plus acid, 5% sugar and 0.1% citric acid]. At both 250 and 500 parts per trillion in the final product, the addition of 4-ethyloctanal was found by the taste panel to have a positive effect on the raspberry, enhancing the natural taste of the raspberry.

EXAMPLE 3

4-Ethyloctanal was added to sugar water [5 weight percent sugar, with 0.1 citric acid] at 3 parts per billion. The water was found to have a flavor similar to aldehyde C-11 which is useful in enhancing citrus flavors.

EXAMPLE 4

4-Ethyloctanal was added to salt water [0.5% NaCl] at a level of 3 parts per billion, which gave the water a very strong fatty lamb taste.

EXAMPLE 5

4-Ethyloctanal was tested with a commercially prepared beef flavor sold by IFF. The 4-ethyloctanal was added at a level of 5 parts per billion to a salt water solution containing 0.03% of the beef flavor. The flavor containing the compound of the present invention was found to have a more fatty meat flavor than the control flavor which did not contain the 4-ethyloctanal.

What is claimed is:

1. A method for improving, enhancing or modifying a flavor of a food product through the addition of an olfactory acceptable amount of 4-ethyloctanal.

2. The method of claim 1 wherein the flavor is incorporated into a food product selected from citrus flavors, berry flavors, meats, gravies, soups, convenience foods, malt, alcoholic and other beverages, milk and dairy products, seafood, candies, vegetables, cereals, soft drinks, snacks, and dog and cat foods.

3. The method of claim 1 wherein the level of 4-ethyloctanal is greater than about 100 parts per trillion by weight in the food product.

4. The method of claim 3 wherein the product is a meat or berry flavor.

5. The method of claim 3 wherein the level is from about 150 parts per trillion to about 10 parts per billion in the food product.

6. The method of claim 3 wherein the level is from about 200 parts per trillion to about 500 parts per trillion in the food product.

7. The method of claim 3 wherein the level is from about 1 to about 10 parts per billion.

* * * * *